(12) United States Patent
Cheng et al.

(10) Patent No.: US 11,638,696 B2
(45) Date of Patent: May 2, 2023

(54) METHOD FOR PREPARING ADDITIVE-FREE CELL-WALL-BROKEN GRANULE OF CHINESE MEDICINAL MATERIAL

(71) Applicant: ZHONGSHAN ZHONGZHI PHARMACEUTICAL GROUP CO., LTD., Guangdong (CN)

(72) Inventors: Jinle Cheng, Guangdong (CN); Zhitian Lai, Guangdong (CN); Jiyin Xu, Guangdong (CN); Yongjun Chen, Guangdong (CN); Wen Deng, Guangdong (CN); Lihua Peng, Guangdong (CN); Weixuan Chen, Guangdong (CN); Jinmei Chen, Guangdong (CN); Yina Wang, Guangdong (CN); Yanling Liang, Guangdong (CN); Weilin Qiao, Guangdong (CN); Xiaojun Cao, Guangdong (CN)

(73) Assignee: ZHONGSHAN ZHONGZHI PHARMACEUTICAL GROUP CO., LTD., Guangdong (CN)

( * ) Notice: Subject to any disclaimer, the term of this patent is extended or adjusted under 35 U.S.C. 154(b) by 269 days.

(21) Appl. No.: 17/075,709

(22) Filed: Oct. 21, 2020

(65) Prior Publication Data
US 2021/0030684 A1 Feb. 4, 2021

Related U.S. Application Data

(63) Continuation of application No. PCT/CN2019/078215, filed on Mar. 15, 2019.

(30) Foreign Application Priority Data

Apr. 25, 2018 (CN) .......................... 201810384021.6

(51) Int. Cl.
*A61K 36/00* (2006.01)
*A61K 9/16* (2006.01)
*A61K 36/481* (2006.01)
*A61K 36/537* (2006.01)
*A61K 36/808* (2006.01)

(52) U.S. Cl.
CPC .......... *A61K 9/1682* (2013.01); *A61K 36/481* (2013.01); *A61K 36/537* (2013.01); *A61K 36/808* (2013.01); *A61K 2236/13* (2013.01); *A61K 2236/15* (2013.01); *A61K 2236/333* (2013.01)

(58) Field of Classification Search
CPC ........................ A61K 2236/15; A61K 2236/13
See application file for complete search history.

(56) References Cited

FOREIGN PATENT DOCUMENTS

| CN | 101147746 A | * | 3/2008 |
|---|---|---|---|
| CN | 101147746 | | 2/2011 |
| CN | 106265802 A | * | 1/2017 |
| CN | 106423490 | | 2/2017 |
| CN | 106423490 A | * | 2/2017 |
| CN | 108310056 | | 7/2018 |

OTHER PUBLICATIONS

Zhaowang Zhang, et al., "Traditional Chinese Medicine Pharmacy." China Press of Traditional Chinese Medicine, Jan. 2003, with partial English translation thereof, pp. 1-810.
"International Search Report (Form PCT/ISA/210)" of PCT/CN2019/078215, dated May 17, 2019, with English translation thereof, pp. 1-4.

* cited by examiner

*Primary Examiner* — Qiuwen Mi
(74) *Attorney, Agent, or Firm* — JCIP Global Inc.

(57) ABSTRACT

The present invention provides a method for preparing an additive-free cell-wall-broken granule of a Chinese medicinal material. The cell-wall-broken granule is obtained by medicinal material concocting and grinding, first cell-wall-breaking and grinding, screening, second wall-breaking and grinding, mixing, pelleting, and granulating and sieving. The obtained granule has a moderate tightness, a relatively rapid dissolution and diffusion and a good uniformity, overcoming problems of a difficulty of dissolution and diffusion and a poor uniformity of the existing cell-wall-broken granules.

9 Claims, 3 Drawing Sheets

METHOD FOR PREPARING ADDITIVE-FREE CELL-WALL-BROKEN GRANULE OF CHINESE MEDICINAL MATERIAL

CROSS-REFERENCE TO RELATED APPLICATION

The present application is a continuation of PCT/CN2019/078215, filed on Mar. 15, 2019, and is related to and claims priority from Chinese patent application no. 201810384021.6, filed on Apr. 25, 2018. The entire contents of the aforementioned application are hereby incorporated by reference herein.

TECHNICAL FIELD

The present invention relates to a method for preparing a cell-wall-broken powder of a Chinese medicinal material.

BACKGROUND

Superfine grinding technology is a new technology that has developed rapidly in recent years. Using a cell-wall-broken grinding technology to grind a Chinese Medicine decoction piece to around 300 mesh, a cell-wall-broken rate can reach 86.7%, which improves a dissolution of an active ingredient in medicinal materials and greatly enhances a pharmacodynamic effect thereof, with a utilization rate of the active ingredient of more than 90%, achieving a reduction of a usage amount of the medicinal materials and a protection of resources of the medicinal materials, and improving a quality of medicines and increasing a pharmacodynamic effect at the same time.

However, most Chinese medicinal materials are natural animals and plants, with complex components, including a variety of small molecule chemical ingredients, macromolecule organic matters (proteins, nucleic acids, lipids and carbohydrates), inorganic matters (such as water, salts and minerals) and cell ergastic substances (metabolites, storage substances, etc.). As the active ingredient that exerts the pharmacodynamic effect at the same time, it is generally a cell ergastic substance with a relatively low content. Moreover, a distribution of a variety of active ingredients in different parts of the medicinal materials or in cells with different constituents in the same part is inconsistent. Medicinal parts of the Chinese medicinal materials are complex, including various medicinal parts such as a flower, a leaf, a root, a stem and the whole plant. Properties of various different medicinal parts differ greatly, from a cell level, various constituent tissues thereof from outside to inside, such as a phellem layer, a cortex, a phloem, a cambium, and a xylem are composed of different types of cells, physical and chemical properties such as a density and a cell-wall-breaking stress of the constituent cells thereof, such as a parenchyma cell, a stone cell, a vessel, a wood fiber, a cork cell and other cells, are different, and thus a cell-wall-breaking property thereof differs greatly. Only through a simple process of cell-wall-breaking and grinding, it is easy to cause that a cell-wall-broken powder obtained in a certain section of a cell-wall-broken material is an ingredient which is easy to be cell-wall-broken with a small particle size, while a certain part is an ingredient hard to be cell-wall-broken with a relatively large particle size, and the distribution of ingredients in the entire cell-wall-broken powder is uneven, which is impossible to obtain an uniform cell-wall-broken powder product with an evenly distributed particle size and active ingredient content, so as to affect the efficacy and safety of clinical medication.

At the same time, as the cell-wall-broken rate of a superfine preparation increases, there are inherent problems such as an increased surface area of the cell-wall-broken preparation, an irregular shape, a poor fluidity and dispersion, a high hygroscopicity, and a poor stability. A current treatment method is to perform pelletization on the superfine cell-wall-broken powder, to increase the stability of the product. A patent application with an application No. 201610596213.4 discloses an ultrasonic cell-wall-breaking method of the Chinese Medicine decoction piece and a device thereof, which solves a problem of a high manufacturing cost of the Chinese Medicine decoction piece. However, there are still problems of a low utilization efficiency of raw materials of the Chinese Medicine decoction piece, a poor cell-wall-breaking uniformity of the raw materials of the Chinese Medicine decoction piece, and a poor stability and a slow dissolution and diffusion rate of the Chinese Medicine decoction piece.

SUMMARY OF THE INVENTION

The present embodiments overcome shortcomings of the prior art, and provides a method for preparing a cell-wall-broken granule, which has a good cell-wall-breaking uniformity, a high stability and a rapid dissolution and diffusion rate.

A method for preparing an additive-free cell-wall-broken granule of a Chinese medicinal material includes the following steps:

(1) medicinal material concocting: picking, washing, slicing and drying the medicinal material to obtain a clean medicinal material;

(2) medicinal material grinding: taking and grinding the clean medicinal material with a mill to obtain an 80-120 mesh medicinal coarse powder;

(3) first wall-breaking and grinding: performing cell-wall-breaking and grinding on the obtained medicinal coarse powder to obtain a 200-1000 mesh cell-wall-broken powder;

(4) particle size screening: screening the cell-wall-broken powder to separate a 300-1000 mesh cell-wall-broken powder;

(5) second cell-wall-breaking and grinding: returning the screened powder with a mesh below 300 to a cell-wall-breaking and grinding cavity for re-grinding to a 300-500 mesh cell-wall-broken powder;

(6) mixing: mixing different materials obtained from two times of the cell-wall-breaking and grinding to obtain a uniform cell-wall-broken powder with different particle sizes and different cell ingredients which are evenly distributed;

(7) pelletizing: placing the cell-wall-broken powder recovered in the step (6) into a mixing agitator, adding a high-concentration ethanol-water solution and a low-concentration ethanol-water solution alternately to make a soft material, extruding with a granulator with a 10-40 mesh sieve to make a wet granule, and drying the made wet granule;

wherein a volume fraction of ethanol in the high-concentration ethanol-water solution is 50%-95%, and a volume fraction of ethanol in the low-concentration ethanol-water solution is 0-30%; and (8) granulating and sieving: granulating and sieving the granule in the step (7) to make a 20-60 mesh granule.

DETAILED DESCRIPTION

Figure 1:
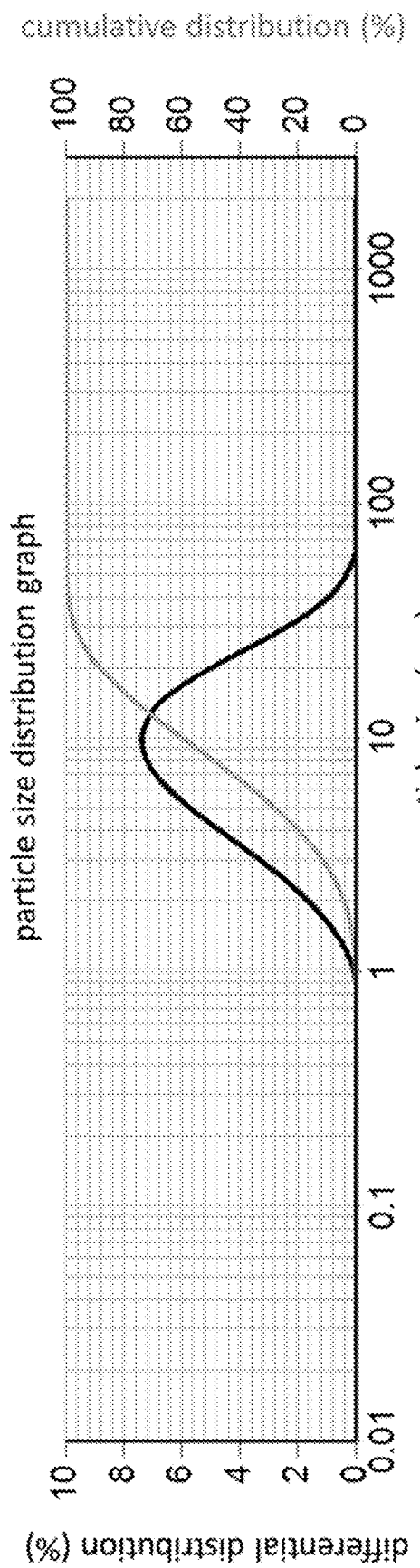
FIG. 1 is a particle size distribution graph of a mixed powder from two times of the cell-wall-breaking of *Astragalus membranaceus* in Embodiment 1.

A method for preparing an additive-free cell-wall-broken granule of a Chinese medicinal material of the present embodiments includes the following steps:

(1) medicinal material concocting: picking, washing, slicing and drying the medicinal material to obtain a clean medicinal material;

(2) medicinal material grinding: taking and grinding the clean medicinal material with a mill to obtain an 80-120 mesh medicinal coarse powder;

(3) first wall-breaking and grinding: performing cell-wall-breaking and grinding on the obtained medicinal coarse powder to obtain a 200-1000 mesh cell-wall-broken powder;

(4) particle size screening: screening the cell-wall-broken powder to separate a 300-1000 mesh cell-wall-broken powder;

(5) second cell-wall-breaking and grinding: returning the screened powder with a mesh below 300 to a cell-wall-breaking and grinding cavity for re-grinding to a 300-500 mesh cell-wall-broken powder;

(6) mixing: mixing different materials obtained from two times of the cell-wall-breaking and grinding to obtain a uniform cell-wall-broken powder with different particle sizes and different cell ingredients which are evenly distributed;

(7) pelletizing: placing the cell-wall-broken powder recovered in the step (6) into a mixing agitator, adding a high-concentration ethanol-water solution and a low-concentration ethanol-water solution alternately to make a soft material, extruding with a granulator with a 10-40 mesh sieve to make a wet granule, and drying the made wet granule;

wherein a volume fraction of ethanol in the high-concentration ethanol-water solution is 50%-95%, and a volume fraction of ethanol in the low-concentration ethanol-water solution is 0-30%; and (8) granulating and sieving: granulating and sieving the granule in the step (7) to make a 20-60 mesh granule.

In the method for preparing the additive-free cell-wall-broken granule of the Chinese medicinal material as mentioned above, after the first cell-wall breaking and grinding, it is screened to make a powder particle size distribution concentrated in 500-600 mesh, and this part of the cell-wall-broken powder is mainly composed of cell-wall-broken parenchyma cells; while the screened powder with a mesh below 300 is performed the second cell-wall-breaking and grinding, making the powder particle size distribution concentrated in 400-500 mesh, and this part of the cell-wall-broken powder is mainly composed of cells with a relatively large grinding stress such as a vessel, a wood fiber and a cork cell. By the operation of performing two times of the cell-wall-breaking and grinding on the medicinal material, the effective grinding of different tissues of the medicinal materials is realized, and the obtained cell-wall-broken powder has a good uniformity, which effectively utilizes resources of Chinese medicines and improves a quality of the medicines.

In the method for preparing the additive-free cell-wall-broken granule of the Chinese medicinal material as mentioned above, a weight ratio of the ethanol-water solution used in the step (7) to a superfine powder is (0.1-0.99):1.

In the method for preparing the additive-free cell-wall-broken granule of the Chinese medicinal material as mentioned above, the weight ratio of the ethanol-water solution used in the step (7) to the superfine powder is (0.3-0.8):1.

In the method for preparing the additive-free cell-wall-broken granule of the Chinese medicinal material as mentioned above, the weight ratio of the ethanol-water solution used in the step (7) to the superfine powder is (0.5-0.7):1.

In the method for preparing the additive-free cell-wall-broken granule of the Chinese medicinal material as mentioned above, in the step (7), when extruding to make the wet granule, a force of the extruding is 0.05-1 MPa and a rotation speed is 40-100 r/min.

In the method for preparing the additive-free cell-wall-broken granule of the Chinese medicinal material as mentioned above, the force of the extruding is 0.25-0.45 MPa and the rotation speed is 75-85 r/min.

In the method for preparing the additive-free cell-wall-broken granule of the Chinese medicinal material as mentioned above, a step of the grinding in the step (3) and the step (5) is performed in a jet mill, a temperature of a grinding space is 18-26° C., a relative humidity is ≤55%, a inlet working pressure is ≥0.7 MPa, and a rotation speed of a grader is 30-35 r/s.

In the method for preparing the additive-free cell-wall-broken granule of the Chinese medicinal material as mentioned above, the volume fraction of the ethanol in the high-concentration ethanol-water solution in the step (7) is 60%-90%, and the volume fraction of the ethanol in the low-concentration ethanol-water solution is 10%-20%.

In the method for preparing the additive-free cell-wall-broken granule of the Chinese medicinal material as mentioned above, the volume fraction of the ethanol in the high-concentration ethanol-water solution in the step (7) is 70%-80%, and the volume fraction of the ethanol in the low-concentration ethanol-water solution is 15%-20%.

The beneficial effects of the present embodiments are as follows:

(1) the Chinese medicinal material is cell-wall-broken and ground to above 300 mesh, with the cell-wall-broken rate above 99%, so that the active ingredient of the medicine can be fully dissolved, saving resources of Chinese medicinal materials;

(2) the Chinese medicinal material is cell-wall-broken and ground twice through the jet mill, and the cell-wall-broken powder has the uniform particle size, the even distribution of various ingredients and the good uniformity; and (3) during the pelletizing process, different concentrations of ethanol-water solutions are added alternately to make the granule, so that the made granule has a good dissolution and diffusion and a rapid disintegration, overcoming problems of a difficulty of dissolution and diffusion and a poor stability of the cell-wall-broken granules in the prior art.

The present invention will be further described in detail below with reference to specific embodiments. Unless otherwise specified, reagents, equipment and methods used in the present embodiments are conventionally commercially available reagents and equipment and conventionally used methods in the art.

Embodiment 1

(1) medicinal material concocting: *Astragalus membranaceus* was picked, washed, sliced and dried to obtain clean *Astragalus membranaceus*;

(2) medicinal material grinding: the clean *Astragalus membranaceus* was taken and ground with a mill with a 100 mesh sieve to obtain an 80-120 mesh *Astragalus membranaceus* coarse powder;

(3) first cell-wall-breaking and grinding: cell-wall-breaking and grinding was performed on the obtained *Astragalus membranaceus* coarse powder to obtain a 200-1000 mesh cell-wall-broken powder;

(4) particle size screening: the cell-wall-broken powder was screened to separate a 300-1000 mesh cell-wall-broken powder, and a powder particle size distribution was concentrated in 500-600 mesh;

(5) second cell-wall-breaking and grinding: the screened powder with a mesh below 300 was returned to a cell-wall-breaking and grinding cavity for re-grinding so that it is cell-wall-broken and ground into a 300-500 mesh cell-wall-broken powder, with the powder particle size distribution concentrated in 400-500 mesh;

(6) mixing: different materials obtained from two times of the cell-wall-breaking and grinding were mixed through a material transfer mixing system;

(7) pelletizing: the cell-wall-broken powder recovered in the step (6) was placed into a mixing agitator, a 90% ethanol-water solution and a 20% ethanol-water solution were added alternately to make a soft material, a total added amount of the ethanol-water solution was 0.5 of a weight of the cell-wall-broken powder, a wet granule was made through extrusion with a granulator with a 30 mesh sieve, and the made wet granule was dried; and (8) granulating and sieving: the granule obtained in the step (7) was granulated and sieved to make a 20-60 mesh granule.

Embodiment 2

According to the preparation method of Embodiment 1, *Salvia miltiorrhiza* was processed to obtain a corresponding *Salvia miltiorrhiza* granule. Differences were that in the step (7), the volume fractions of the high concentration ethanol-water solution and the low concentration ethanol-water solution were 75% and 30%, respectively, and the total added amount of the ethanol-water solution was 0.3 of the weight of the cell-wall-broken powder, and a 40 mesh sieve was selected for the pelletizing through the extrusion.

Embodiment 3

According to the preparation method of Embodiment 1, *Radix scrophulariae* was processed to obtain a corresponding *Radix scrophulariae* granule. Differences were that in the step (7), the volume fractions of the high concentration ethanol-water solution and the low concentration ethanol-water solution were 60% and 10%, respectively, and the total added amount of the ethanol-water solution was 0.8 of the weight of the cell-wall-broken powder, and a 20 mesh sieve was selected for the pelletizing through the extrusion.

Comparative Example 1

(1) medicinal material concocting: *Astragalus membranaceus* was picked, washed, sliced and dried to obtain clean *Astragalus membranaceus*;

(2) medicinal material grinding: the clean *Astragalus membranaceus* was taken and grinded with a mill with a 100 mesh sieve to obtain an 80-120 mesh *Astragalus membranaceus* coarse powder;

(3) first cell-wall-breaking and grinding: ultrasonic cell-wall-breaking and grinding was performed on the obtained *Astragalus membranaceus* coarse powder to obtain a 50-80 µm cell-wall-broken powder;

(4) second cell-wall-breaking and grinding: the cell-wall-broken powder obtained in the step (3) was super-finely ground so that it is cell-wall-broken and ground into a 500-600 mesh wall-broken powder;

(5) mixing: different materials obtained from two times of the cell-wall-breaking and grinding were mixed;

(6) pelletizing: the cell-wall-broken powder recovered in the step (5) was placed into a mixing agitator, a 90% ethanol-water solution and a 20% ethanol-water solution were added alternately to make a soft material, a total added amount of the ethanol-water solution was 0.5 of a weight of the cell-wall-broken powder, a wet granule was made through extrusion with a granulator with a 30 mesh sieve, and the made wet granule was dried; and (7) granulating and sieving: the granule in the step (6) was granulated and sieved to make a 20-60 mesh granule.

Comparative Example 2

(1) medicinal material concocting: *Astragalus membranaceus* was picked, washed, sliced and dried to obtain clean *Astragalus membranaceus*;

(2) medicinal material grinding: the clean *Astragalus membranaceus* was taken and ground with a mill with a 100 mesh sieve to obtain an 80-120 mesh *Astragalus membranaceus* coarse powder;

(3) cell-wall-breaking and grinding: cell-wall-breaking and grinding was performed on the obtained *Astragalus membranaceus* coarse powder to obtain a cell-wall-broken powder with a mesh above 300;

(4) preparation of a soft material of the cell-wall-broken powder: the obtained cell-wall-broken powder was placed into a trough-type mixer, a suitable amount of 80-99% ethanol was added to make a soft material;

(5) granule preparation: a small amount of the *Astragalus membranaceus* cell-wall-broken powder obtained in the step (3) was placed into a swing-type pelletor first, a 30-mesh sieve was used to pelletize a granule, in the granule preparation, as the cell-wall-broken powder soft material made in the step (4) was added, the *Astragalus membranaceus* cell-wall-broken powder obtained in the step (3) was added, and a ratio of the soft material to the dry powder was 6:0.5; and (6) a qualified cell-wall-broken decoction piece granule was put into an oven at 50° C.-60° C. for drying, after drying, an oscillating granulator with a 20 mesh sieve in an upper layer and a 60 mesh sieve in a bottom layer was used to granulate and sieve for three times, after sub-packaging, a *Astragalus membranaceus* cell-wall-broken granule was obtained.

Comparative Example 3

(1) medicinal material concocting: *Astragalus membranaceus* was picked, washed, sliced and dried to obtain clean *Astragalus membranaceus*;

(2) medicinal material grinding: the clean *Astragalus membranaceus* was taken and ground with a mill with a 100 mesh sieve to obtain an 80-120 mesh *Astragalus membranaceus* coarse powder;

(3) first cell-wall-breaking and grinding: cell-wall-breaking and grinding was performed on the obtained *Astragalus membranaceus* coarse powder to obtain a 200-1000 mesh cell-wall-broken powder;

(4) particle size screening: the cell-wall-broken powder was screened to separate a 300-1000 mesh cell-wall-broken powder, and a powder particle size distribution was concentrated in 500-600 mesh;

(5) second cell-wall-breaking and grinding: the screened powder with a mesh below 300 was returned to a cell-wall-breaking and grinding cavity for re-grinding so that it is cell-wall-broken and ground into a 300-500 mesh cell-wall-broken powder, with the powder particle size distribution concentrated in 400-500 mesh;

(6) mixing: different materials obtained from two times of the cell-wall-breaking and grinding were mixed through a material transfer mixing system;

(7) pelletizing: the cell-wall-broken powder recovered in the step (6) was placed into a mixing agitator, an ethanol-water solution with a volume fraction of 20% was added alternately to make a soft material, a total added amount of the ethanol-water solution was 0.5 of a weight of the cell-wall-broken powder, a wet granule was made through extrusion with a granulator with a 30 mesh sieve, and the made wet granule was dried; and (8) granulating and sieving: the granule obtained in the step (7) was granulated and sieved to make a 20-60 mesh granule.

Comparative Example 4

(1) medicinal material concocting: *Astragalus membranaceus* was picked, washed, sliced and dried to obtain clean *Astragalus membranaceus*;

(2) medicinal material grinding: the clean *Astragalus membranaceus* was taken and ground with a mill with a 100 mesh sieve to obtain an 80-120 mesh *Astragalus membranaceus* coarse powder;

(3) first cell-wall-breaking and grinding: cell-wall-breaking and grinding was performed on the obtained *Astragalus membranaceus* coarse powder to obtain a 200-1000 mesh cell-wall-broken powder;

(4) particle size screening: the cell-wall-broken powder was screened to separate a 300-1000 mesh cell-wall-broken powder, and a powder particle size distribution was concentrated in 500-600 mesh;

(5) second cell-wall-breaking and grinding: the screened powder with a mesh below 300 was returned to a cell-wall-breaking and grinding cavity for re-grinding so that it is cell-wall-broken and ground into a 300-500 mesh cell-wall-broken powder, with the powder particle size distribution concentrated in 400-500 mesh;

(6) mixing: different materials obtained from two times of the cell-wall-breaking and grinding were mixed through a material transfer mixing system;

(7) pelletizing: the cell-wall-broken powder recovered in the step (6) was placed into a mixing agitator, an ethanol-water solution with a volume fraction of 60% was added alternately to make a soft material, a total added amount of the ethanol-water solution was 0.5 of a weight of the cell-wall-broken powder, a wet granule was made through extrusion with a granulator with a 30 mesh sieve, and the made wet granule was dried; and (8) granulating and sieving: the granule obtained in the step (7) was granulated and sieved to make a 20-60 mesh granule.

Comparative Example 5

(1) medicinal material concocting: *Astragalus membranaceus* was picked, washed, sliced and dried to obtain clean *Astragalus membranaceus*;

(2) medicinal material grinding: the clean *Astragalus membranaceus* was taken and ground with a mill with a 100 mesh sieve to obtain an 80-120 mesh *Astragalus membranaceus* coarse powder;

(3) first cell-wall-breaking and grinding: cell-wall-breaking and grinding was performed on the obtained *Astragalus membranaceus* coarse powder to obtain a 200-1000 mesh cell-wall-broken powder;

(4) particle size screening: the cell-wall-broken powder was screened to separate a 300-1000 mesh cell-wall-broken powder, and a powder particle size distribution was concentrated in 500-600 mesh;

(5) second cell-wall-breaking and grinding: the screened powder with a mesh below 300 was returned to a cell-wall-breaking and grinding cavity for re-grinding so that it is cell-wall-broken and ground into a 300-500 mesh cell-wall-broken powder, with the powder particle size distribution concentrated in 400-500 mesh;

(6) mixing: different materials obtained from two times of the cell-wall-breaking and grinding were mixed through a material transfer mixing system;

(7) pelletizing: the cell-wall-broken powder recovered in the step (6) was placed into a mixing agitator, an ethanol-water solution with a volume fraction of 90% was added alternately to make a soft material, a total added amount of the ethanol-water solution was 0.5 of a weight of the cell-wall-broken powder, a wet granule was made through extrusion with a granulator with a 30 mesh sieve, and the made wet granule was dried; and (8) granulating and sieving: the granule obtained in the step (7) was granulated and sieved to make a 20-60 mesh granule.

Particle Size Uniformity Detection Test

The mixed powders obtained from two times of the cell-wall-breaking in Embodiment 1 to Embodiment 3 and the cell-wall-broken powders obtained in Comparative Example 1 and Comparative Example 2 were taken to measure sizes of the cell-wall-broken powder particles by a laser particle size analyzer. Results are shown in Table 1.

TABLE 1

Detection results of sizes of cell-wall-broken powder particles

| | Characteristic particle size (μm) | | | | | | |
|---|---|---|---|---|---|---|---|
| | D10 | D25 | D50 | D75 | D90 | D95 | D99 |
| Embodiment 1 | 2.815 | 4.634 | 8.150 | 13.824 | 21.024 | 35.483 | 41.670 |
| Embodiment 2 | 3.816 | 6.498 | 11.124 | 18.196 | 27.448 | 35.556 | 37.489 |
| Embodiment 3 | 3.966 | 6.349 | 10.267 | 15.993 | 23.061 | 28.251 | 39.277 |
| Comparative Example 1 | 3.899 | 7.028 | 13.243 | 24.717 | 45.090 | 109.157 | 154.485 |
| Comparative Example 2 | 5.379 | 11.540 | 24.723 | 49.950 | 109.687 | 143.506 | 175.672 |

It can be seen from data in Table 1 that the cell-wall-broken powder obtained by the grinding method provided by the present embodiment has an even particle size and a better uniformity.

Figure 2:
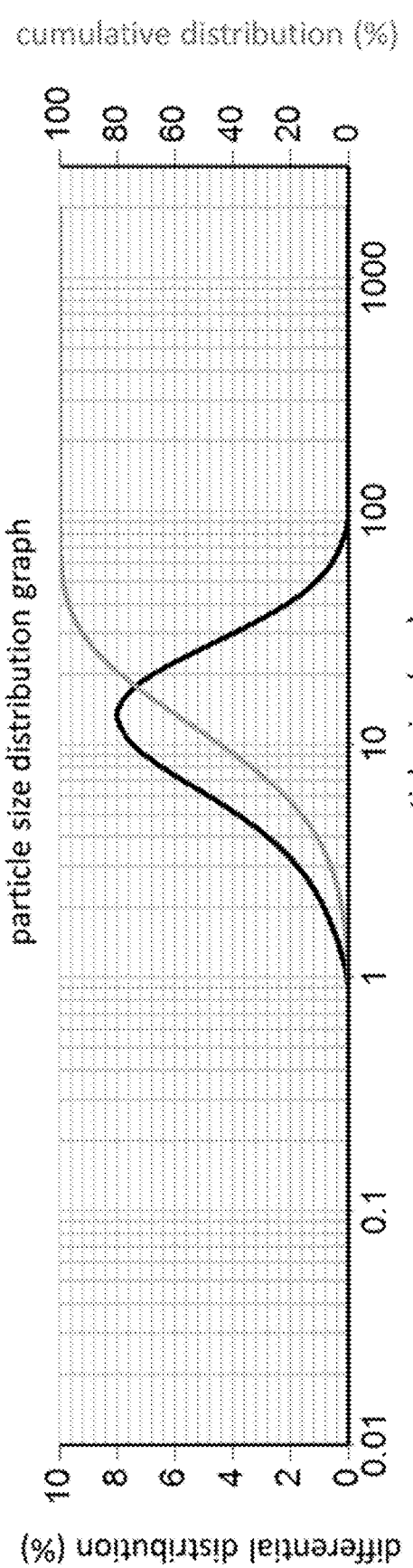
FIG. 2 is a particle size distribution graph of a mixed powder from two times of the cell-wall-breaking of *Salvia miltiorrhiza* in Embodiment 2.
Figure 3:
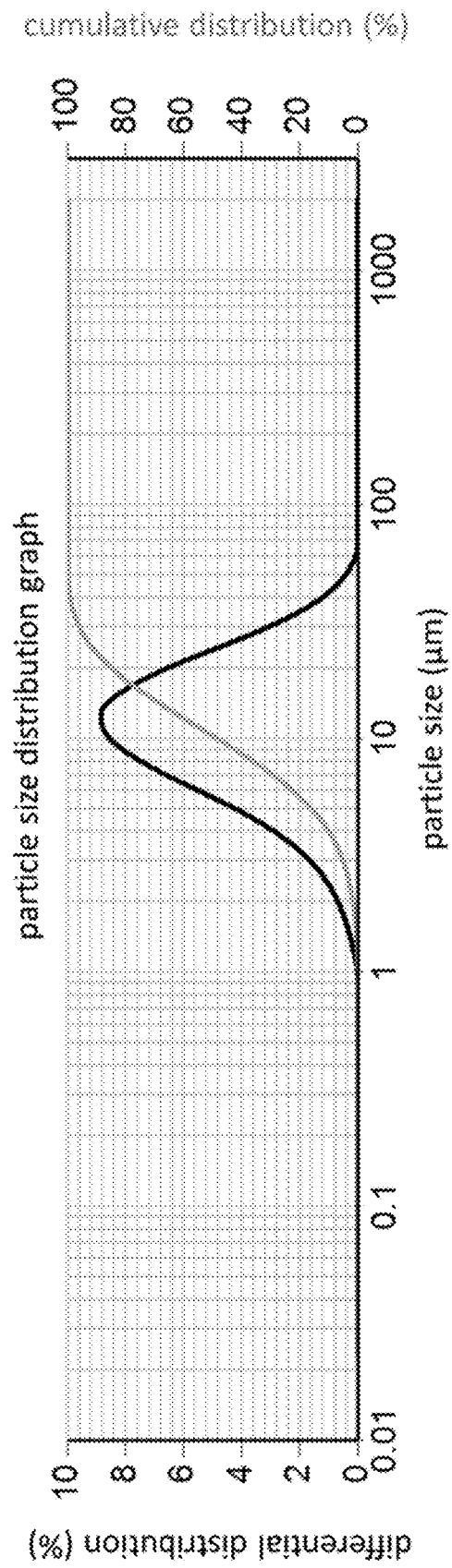
FIG. 3 is a particle size distribution graph of a mixed powder from two times of the cell-wall-breaking of *Radix scrophulariae* in Embodiment 3.
Figure 4:
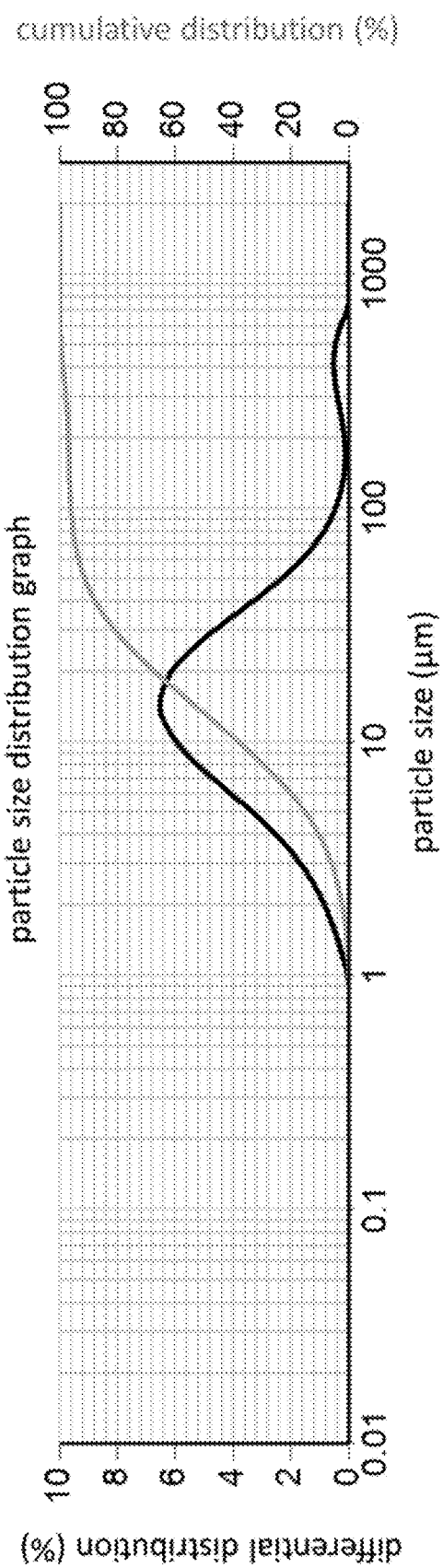
FIG. 4 is a particle size distribution graph of a cell-wall-broken powder of *Astragalus membranaceus* in Comparative example 1.
Figure 5:
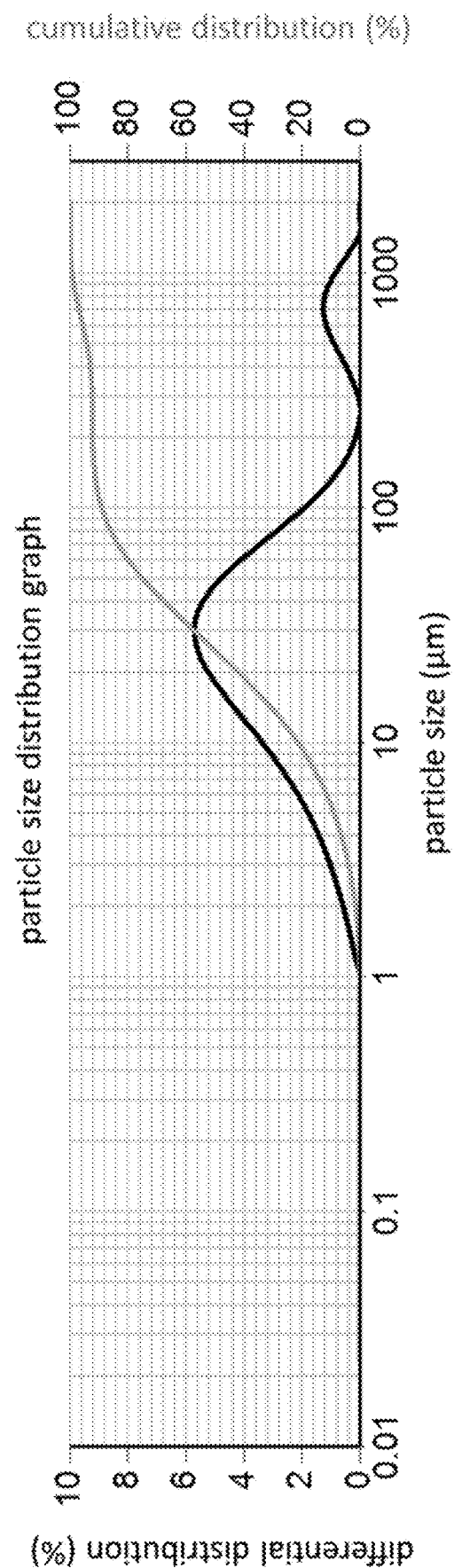
FIG. 5 is a particle size distribution graph of a cell-wall-broken powder of *Astragalus membranaceus* in Comparative example 2.

Through statistics of the particle size distribution of Embodiment 1 to Embodiment 3, results are shown in FIGS. 1-3. The particle size of the cell-wall-broken powder is in a normal distribution and the particle size is even with a good uniformity.

Ingredient uniformity detection test Three parts of the *Radix scrophulariae* cell-wall-broken granule in Embodiment 3 were randomly selected, and active ingredients in the powder, harpagide and harpagoside, were measured by High Performance Liquid Chromatography (General Principle 0512), with octadecylsilane chemically bonded silica as a filler; acetonitrile was used as a mobile phase A, and a 0.03% phosphoric acid solution as a mobile phase B, to perform a gradient elution as specified in the following table; and a detection wavelength was 210 nm. A number of theoretical plates should not be less than 5000 according to peaks of harpagoside and harpagide.

| Time (min) | Mobile phase A (%) | Mobile phase B (%) |
|---|---|---|
| 0 to 10 | 3→10 | 97→90 |
| 10 to 20 | 10→33 | 90→67 |
| 20 to 25 | 33→50 | 67→50 |
| 25 to 30 | 50→80 | 50→20 |
| 30 to 35 | 80 | 20 |
| 35 to 37 | 80→3 | 20→97 |

Preparation of a reference substance solution was that an appropriate amount of a harpagide reference substance and an appropriate amount of a harpagoside reference substance were taken and accurately weighed, with 30% methanol added to prepare a mixed solution containing 60 μg harpagide and 20 μg harpagoside per 1 ml, and the reference substance solution was obtained.

Preparation of a test substance solution was that the three parts of the *Radix scrophulariae* cell-wall-broken powder in Embodiment 3 (through a No. 3 sieve), 0.5 g×3, were randomly selected, accurately weighed, and placed in a conical flask with a stopper, with 50 ml of 50% ethanol accurately added, closely stoppered, weighed, soaked for 1 hour, with a ultrasonic treatment (power of 500 W, frequency of 40 kHz) for 45 minutes, cooled and weighed again, with 50% ethanol to make up for a lost weight, well shook, and filtered to take a subsequent filtrate, and the test substance solution was obtained.

According to a determination method, 10 μl of the reference substance solution and 10 μl of the test substance solution were accurately taken and injected into a liquid chromatographer for measurement.

A total amount of harpagide ($C_{15}H_{24}O_{10}$) and harpagoside ($C_{24}H_{30}O_{11}$) contained in this product shall not be less than 0.45%, calculated on the anhydrous substance.

The total amounts of harpagide ($C_{15}H_{24}O_{10}$) and harpagoside ($C_{24}H_{30}O_{11}$) in the three samples were determined to be 0.65%, 0.63%, and 0.63%, respectively, with an RSD of 1.81%.

It can be seen that contents of the active ingredients in the three samples randomly weighed are similar, so the mixed cell-wall-broken powder obtained from two times of the cell-wall-breaking has good particle uniformity, which ensures a stability of a medicine quality.

Dissolution and Diffusion Time Detection Test

Test method: 2 g of each of the dry granules obtained in Embodiment 1 to Embodiment 3 and Comparative Example 1 to Comparative Example 5 were accurately weighed, placed in a 300 ml transparent cup, with 100 ml of water at 90° C. to 95° C. added (without heating during shaking), a dissolution and diffusion status of the granules in the cup was checked after shaking clockwise at a speed of 1 circle per second for 1 minute, 2 minutes, 3 minutes, 5 minutes, 10 minutes; and another 0.5 ml of liquid in the cup was taken to detect a shading rate with a laser particle size analyzer. Test results are shown in Table 2 below.

TABLE 2

Dissolution and diffusion test results of the cell-wall-broken granules

| | Shading rate (%) | | | | | | | |
|---|---|---|---|---|---|---|---|---|
| | Embodiment 1 | Embodiment 2 | Embodiment 3 | Comparative Example 1 | Comparative Example 2 | Comparative Example 3 | Comparative Example 4 | Comparative Example 5 |
| 1 min | 1.76 | 1.35 | 1.47 | 0.98 | 1.35 | 0.12 | 1.27 | 1.34 |
| 2 min | 4.72 | 4.33 | 4.51 | 3.27 | 3.57 | 0.34 | 4.31 | 3.58 |

TABLE 2-continued

Dissolution and diffusion test results of the cell-wall-broken granules

Shading rate (%)

|  | Embodiment 1 | Embodiment 2 | Embodiment 3 | Comparative Example 1 | Comparative Example 2 | Comparative Example 3 | Comparative Example 4 | Comparative Example 5 |
|---|---|---|---|---|---|---|---|---|
| 3 min | 6.38 | 5.94 | 6.23 | 5.08 | 5.74 | 0.47 | 5.15 | 5.71 |
| 5 min | 8.96 | 9.43 | 9.62 | 6.98 | 7.65 | 0.65 | 8.56 | 7.68 |
| 10 min | 12.57 | 12.06 | 12.23 | 10.96 | 11.39 | 0.83 | 10.02 | 11.40 |

The data in Table 2 show that the method for preparing cell-wall-broken granules provided by the present embodiment has better effects and a more rapid dissolution and diffusion rate. The only difference between Comparative Example 3 to Comparative Example 5 and Embodiment 1 is that ethanol-water solutions with volume fractions of 20%, 60% and 90% were used respectively as a wetting agent for pelletizing, and results showed that dissolution and diffusion of the cell-wall-broken granule of Comparative Example 3 to Comparative Example 5 is worse compared with Embodiment 1.

The foregoing descriptions are only preferred embodiments of the present invention, and are not intended to limit the present invention. For those skilled in the art, the present invention can have various modifications and variations. Any modification, equivalent replacement, improvement, etc., made within the spirits and principles of the present invention shall be included in the scope of protection of the present invention.

What is claimed is:

1. A method for preparing an additive-free cell-wall-broken granule of a Chinese medicinal material comprising the following steps:
   (1) medicinal material concocting: picking, washing, slicing and drying a medicinal material to obtain a clean medicinal material;
   (2) medicinal material grinding: taking and grinding the clean medicinal material with a mill to obtain an 80-120 mesh medicinal coarse powder;
   (3) first cell-wall-breaking and grinding: performing cell-wall-breaking and grinding on the obtained medicinal coarse powder to obtain a 200-1000 mesh cell-wall-broken powder;
   (4) particle size screening: screening the cell-wall-broken powder to separate a 300-1000 mesh cell-wall-broken powder;
   (5) second cell-wall-breaking and grinding: returning the screened powder with a mesh below 300 to a cell-wall-breaking and grinding cavity for re-grinding so that it is cell-wall-broken and ground into a 300-500 mesh cell-wall-broken powder;
   (6) mixing: mixing different materials obtained from two times of the cell-wall-breaking and grinding to obtain a uniform cell-wall-broken powder with different particle sizes and different cell ingredients which are evenly distributed;
   (7) pelleting: placing the cell-wall-broken powder recovered in the step (6) into a mixing agitator, adding a high-concentration ethanol-water solution and a low-concentration ethanol-water solution alternately to make a soft material, wherein the volume fraction of the ethanol in the high-concentration ethanol-water solution is 60%-90%, and the volume fraction of the ethanol in the low-concentration ethanol-water solution is 10%-20%, and extruding with a granulator with a 10-40 mesh sieve to make a wet granule, and drying the made wet granule;
   and
   (8) granulating and sieving: granulating and sieving the granule in the step (7) to make a 20-40 mesh granule.

2. The method for preparing the additive-free cell-wall-broken granule of the Chinese medicinal material according to claim 1, wherein in the step (4), the screening is performed on the cell-wall-broken powder in a force field to separate the 300-1000 mesh cell-wall-broken powder.

3. The method for preparing the additive-free cell-wall-broken granule of the Chinese medicinal material according to claim 1, wherein a weight ratio of the ethanol-water solution used in the step (7) to a superfine powder is (0.1-0.99):1.

4. The method for preparing the additive-free cell-wall-broken granule of the Chinese medicinal material according to claim 1, wherein in the step (7), when extruding to make the wet granule, a force of the extruding is 0.05-1 MPa and a rotation speed is 40-100 r/min.

5. The method for preparing the additive-free cell-wall-broken granule of the Chinese medicinal material according to claim 4, wherein the force of the extruding is 0.25-0.45 MPa and the rotation speed is 75-85 r/min.

6. The method for preparing the additive-free cell-wall-broken granule of the Chinese medicinal material according to claim 1, wherein a step of the grinding in the step (3) and the step (5) is performed in a jet mill, a temperature of a grinding space is 18-26° C., a relative humidity is ≤55%, an inlet working pressure is ≥0.7 MPa, and a rotation speed of a grader is 30-35 r/s.

7. The method for preparing the additive-free cell-wall-broken granule of the Chinese medicinal material according to claim 1, wherein the volume fraction of the ethanol in the high-concentration ethanol-water solution in the step (7) is 70%-80%, and the volume fraction of the ethanol in the low-concentration ethanol-water solution is 15%-20%.

8. The method for preparing the additive-free cell-wall-broken granule of the Chinese medicinal material according to claim 2, wherein in the step (7), when extruding to make the wet granule, a force of the extruding is 0.05-1 MPa and a rotation speed is 40-100 r/min.

9. The method for preparing the additive-free cell-wall-broken granule of the Chinese medicinal material according to claim 8, wherein the force of the extruding is 0.25-0.45 MPa and the rotation speed is 75-85 r/min.

* * * * *